United States Patent [19]

Hewson

[11] Patent Number: 4,683,890
[45] Date of Patent: Aug. 4, 1987

[54] METHOD AND APPARATUS FOR CONTROLLED BREATHING EMPLOYING INTERNAL AND EXTERNAL ELECTRODES

[75] Inventor: Carl E. Hewson, Marshfield, Mass.

[73] Assignee: Brunswick Manufacturing Co., Inc., North Quincy, Mass.

[21] Appl. No.: 914,244

[22] Filed: Oct. 2, 1986

Related U.S. Application Data

[63] Continuation of Ser. No. 812,015, Dec. 23, 1985, abandoned.

[51] Int. Cl.⁴ ............................................. A61N 1/36
[52] U.S. Cl. .............................. 128/419 PG; 128/786
[58] Field of Search ....... 128/419 D, 419 G, 419 PG, 128/715, 784–786, 421

[56] References Cited

U.S. PATENT DOCUMENTS

| | | | |
|---|---|---|---|
| 3,411,507 | 11/1968 | Wingrove | 128/784 X |
| 3,614,955 | 10/1971 | Mirowski | 128/419 D |
| 3,804,098 | 4/1974 | Friedman | 128/786 |
| 4,088,138 | 5/1978 | Diack et al. | 128/419 D |
| 4,161,952 | 7/1979 | Kinney et al. | 128/786 |
| 4,176,660 | 12/1979 | Mylrea et al. | 128/715 X |
| 4,198,963 | 4/1980 | Barkalow et al. | 128/419 D X |
| 4,351,330 | 9/1982 | Scarberry | 128/419 D X |
| 4,574,807 | 3/1986 | Hewson et al. | 128/768 X |

FOREIGN PATENT DOCUMENTS

| | | | |
|---|---|---|---|
| 0467124 | 8/1950 | Canada | 128/419 G |
| 2493154 | 5/1982 | France | 128/419 G |

OTHER PUBLICATIONS

Nochomovitz; "Electrical Activation of Respiration"; *Engineering in Med. and Biol. Med. Magazine*, 6-1963, pp. 27–31.

*Primary Examiner*—Kyle L. Howell
*Assistant Examiner*—Angela D. Sykes
*Attorney, Agent, or Firm*—Wolf, Greenfield & Sacks

[57] ABSTRACT

The invention relates to apparatus for inducing humans to breathe and comprises a first internal electrode having a contact which is disposed in the lower portion of the esophagus, and second and third external electrodes which are placed over the left and right sides of the chest on the pectoral muscles in the area of the nipples above the rib cage. An electrical circuit is connected to the electrodes and imposes a pulsed charge between the internal and external electrodes which stimulates the muscles of the diaphragm causing the patient's lungs to expand, which is the same as taking a breath. The pulsed charges will be at the rate of approximately 10 to 18 pulses per minute. With a pulse rate of 12 per minute each pulse increases from zero to maximum in approximately two seconds, followed by a drop to zero with a dwell period of approximately three seconds. The pulse is limited to approximately 100 milliamperes and a selected variable voltage of up to 50 volts.

13 Claims, 5 Drawing Figures

METHOD AND APPARATUS FOR CONTROLLED BREATHING EMPLOYING INTERNAL AND EXTERNAL ELECTRODES

RELATED APPLICATION

This application is a continuation of my copending application Ser. No. 812,015, filed Dec. 23, 1985, now abandoned entitled Method and Apparatus for Controlled Breathing Employing Internal and External Electrodes.

INTRODUCTION

This invention relates to a method and apparatus for ventilating patients. When a person's breathing stops due to cardiac arrest or fibrillation, or he suffers respiratory depression from such causes as drug overdose, smoke inhalation, drowning etc., or breathing stops for any other reason, it is imperative to reinstate breathing as a life saving measure as well as to avoid brain damage due to oxygen deficiency.

The normal method of artificially ventilating a patient is to blow air into the lungs in a rhythmic fashion either by mouth to mouth or using an oxygen powered demand valve and mask. Both of these well-known techniques have been used successfully countless times, but they do have certain disadvantages. These techniques create positive pressure in the lungs of the patient being ventilated, and the positive pressure can impair blood flow to the lungs and the return of the blood supply to the heart.

One important object of the present invention is to provide a method and apparatus for ventilating patients which mirrors the normal breathing cycle so as not to inhibit blood flow in the lungs and to the heart.

Another important object of this invention is to provide a non-invasive technique for electrically stimulating natural ventilation.

To accomplish these and other objects in accordance with this invention, by the proper placement of electrodes and by supplying a controlled electrical impulse the diaphragm muscles are stimulated to expand the lungs creating negative pressure causing air to fill the lungs. This is the normal breathing process and it does not inhibit blood flow in the lungs and to the heart. The present invention includes an internal electrode which is passed down the esophagus. The electrode is a tube or rod having a flexibility similar to a normal commercial gastric tube and has a series of circumferential electrical contact rings spaced a few centimeters apart but all electrically connected. Two external electrodes electrically connected together, and each a commercially available ECG electrode, are placed one left and one right on the body of the patient in the region of the nipples above the rib cage. Between the internal and two external electrodes is passed a selectable pulsed current up to 100 miliamperes selectively delivered at from 10 to 18 cycles per minute. A typical pulse for a rate of 12 pulses per minute would be a linear rise from zero output to maximum output in 2 seconds followed by a zero output for the next three seconds. The cycle is repeated so long as the stimulation is needed. The electrical circuit is battery operated and the device may be handheld.

These and other object and features of this invention will be better understood and appreciated from the following detailed description of one embodiment thereof, selected for purposes of illustration and shown in the accompanying drawings.

BRIEF FIGURE DESCRIPTION

DETAILED DESCRIPTION

The action of breathing, which consists of two functions, namely inspiration and exhalation, may be described as follows:

The diaphragm is the principal muscle of inspiration. When in a condition of rest the muscle presents a domed surface, concave toward the abdomen and consists of circumferential muscle and a central tendinous part. When the muscle fibres contract, they become less arched, or nearly straight, and thus cause the central tendon to descend and become a fixed point and enables the circumferential muscles to act from it and so elevate the lower ribs and expand the thoracic cavity. The ordinary action of expiration is hardly effected by muscular forces but results from a return of the walls of the thorax to a condition of rest owing to their own elasticity and to that of the lungs. (See Anatomy by Henry S. Gray, Bounty Books, published in 1977, page 555.)

The present invention artificially stimulates the diaphragm muscle to duplicate the action which occurs naturally in a healthy person.

Figure 1:
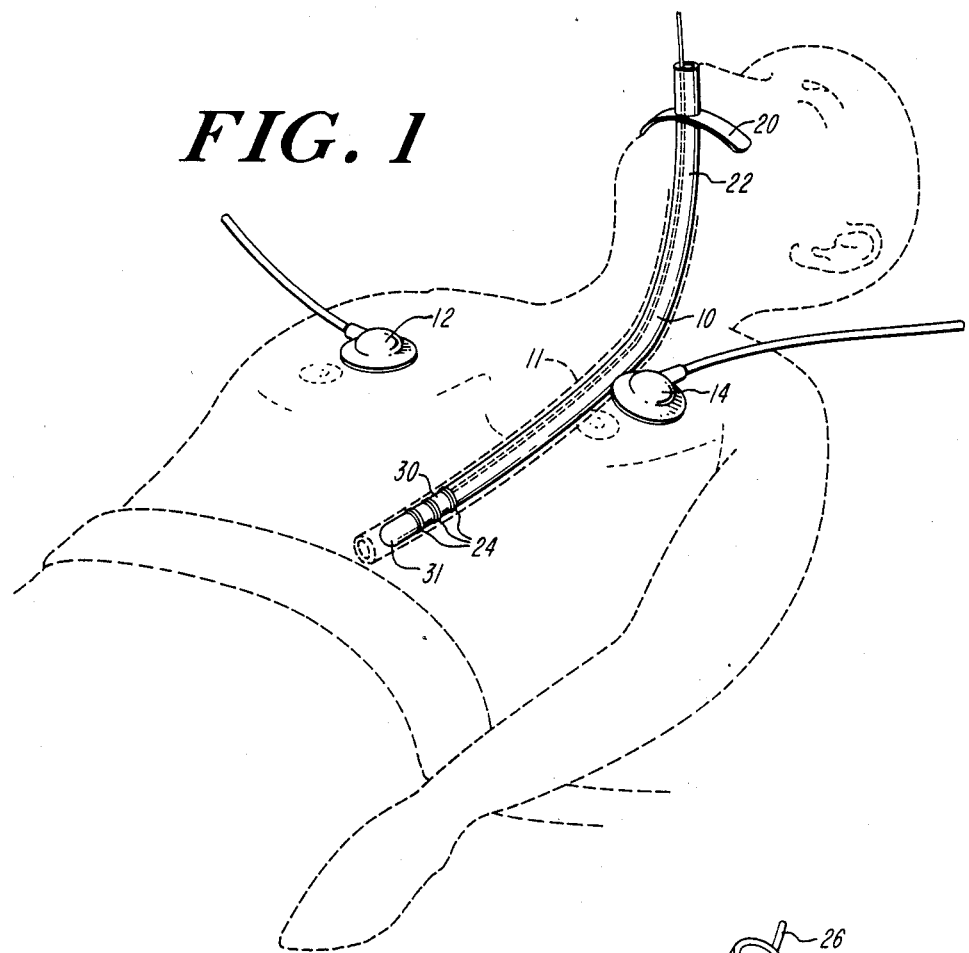
FIG. 1 is a cross-sectional view, somewhat diagrammatic, of the head and chest of a patient and showing the use of the present invention.

FIG. 1 depicts a patient being assisted by the ventilating system of the present invention. A first electrode 10 is shown disposed in the patient's esophagus 11 and a pair of external electrodes 12 and 14 are shown placed on the patient's chest on the left and right sides in the region of the nipples and above the rib cage. The electrodes are all connected to an electrical circuit 16 which impresses a pulsed charge between the internal electrode 10 and the external electrodes 12 and 14 through the diaphragm muscle of the patient. When the diaphragm muscle is stimulated by the charge, the muscles contract so as to elevate the lower ribs and expand the thoracic cavity, which effects a reduction in pressure in turn causing inspiration. When the charge is removed, the walls of the thorax return to the rest condition causing exhalation.

Figure 2:
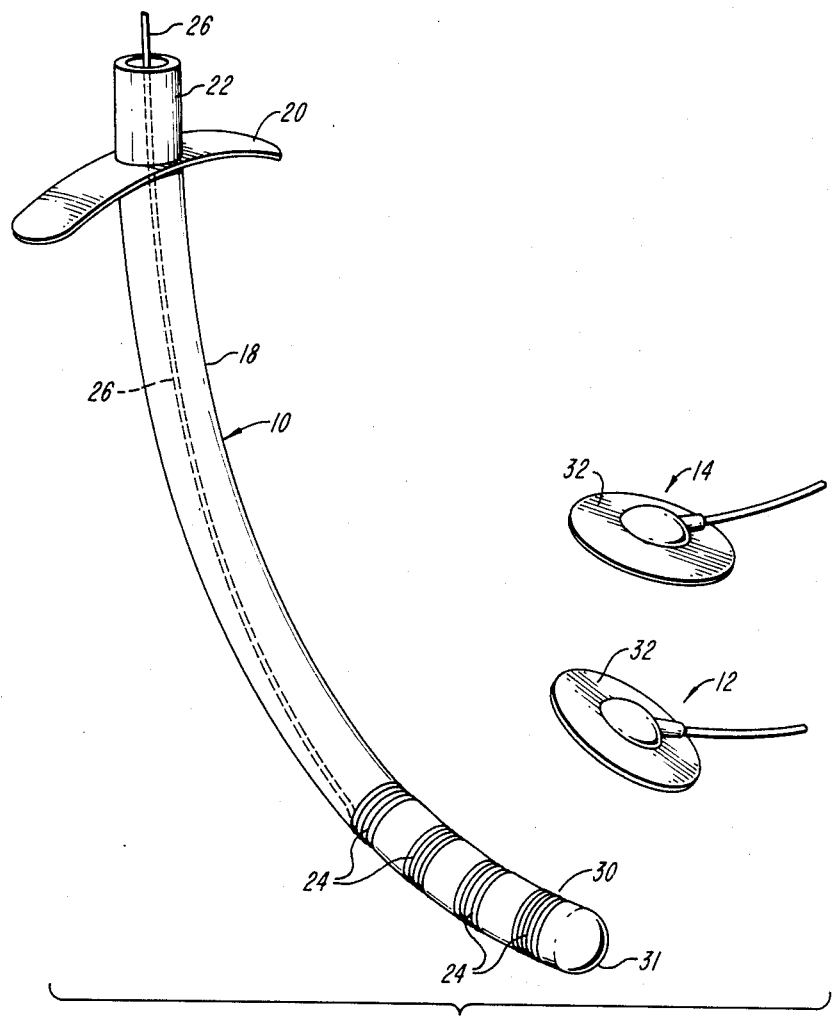
FIG. 2 is a perspective view of the invention shown in FIG. 1.

In FIGS. 1 and 2 the electrode 10 is shown to include a curved tubular body 18 which is shaped to be inserted directly into the patient's esophagus without the aid of a larger tubular member serving as a guide for that purpose. It is to be understood, however, that the system of the present invention may be used in combination with other apparatus and it is contemplated that the electrode 10 in certain situations may be guided into the esophagus through a previously inserted tube such as a gastric tube. The electrode 10 carries a stop 20 adjacent to its proximal end 22 which may be used to limit the depth of penetration of the electrode 10 into the esophagus. The stop 20 should not cover the mouth or otherwise interfere with the passage of air to and from the lungs. The body 18 of the electrode preferably is somewhat flexible in the nature of a commercially available gastric tube so that it may be inserted in the esophagus and will not injure the esophagus lining. It may or may not call for the use of lubricant. Moreover, the electrode may be inserted through the mouth or nose. The electrode may be identical to that shown in copending application Ser. No. 585,761 filed Mar. 2, 1984 entitled Heart Pacer, which application has a common assignee with this application.

Figure 3:
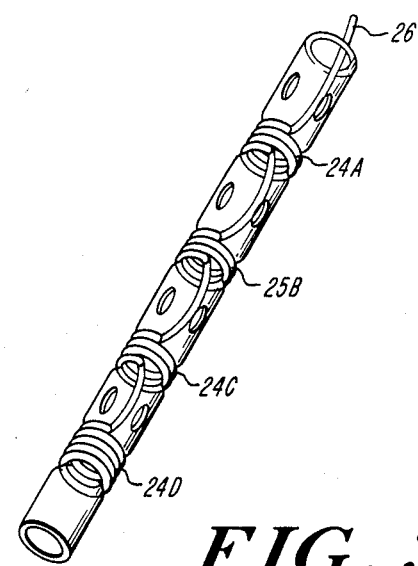
FIG. 3 is an enlarged perspective view of the distal end of the internal electrode forming part of this invention.

In FIG. 3 the distal end of the electrode 10 is shown in detail. It includes four contact rings 24 embedded in its surface. While four rings are shown, a lesser or greater number may be used. The contact rings in the embodiment shown are formed from a continuous length of tinned copper wire 26 which is connected to a post contact 28 shown on the proximal end 22 of the body 18 which in turn is connected during use to the electrical control system 16. The wire 26 extends inside the body 18 to first ring contact 24A in turn formed by several turns of wire on the surface of the body 18. The wire again enters the body 18 beyond the contact 24A and reemerges at the next ring contact 24B also formed by several additional turns of the wire. The third and fourth ring contacts 24C and 24D are similarly formed and connected to one another by the wire inside the body. Thus, the four electrode contacts are connected in series and formed from a single length of wire. Typically, each of the ring contacts may be 0.2 inch in length and they may be spaced one inch apart. The wire may typically be 24 gauge. The distal end 30 of the body is provided with a smooth rounded tip 31 which will slide smoothly down the esophagus or guide tube (if used).

When the electrode 10 is used to stimulate breathing, the distal end 30 is positioned so that the several ring contacts 24 lie in the lower third of the esophagus. The stop 20 ensures proper positioning of the electrode.

The external electrodes 12 and 14 are identical and may be like those used in electrocardiogram machines. Each includes a flat circular pad 32 with a post contact 34 on its upper surface connected to electrical contact 36 on its lower surface. A conducting gelatin is applied to the contact 36 when in use to make good electrical contact with the patient's skin. The under surface of the pads 32 may also carry an adhesive to secure the electrodes in place on the patient's chest on each side, in the region of the nipples adjacent the rib cage. The post contacts 34 may be engaged by snaps 38 which connect electrodes 10 and 12 to the electrical circuit 16.

Figure 5:
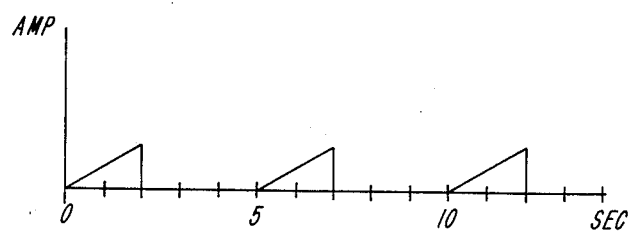
FIG. 5 is a chart of the pulse impressed upon the patient in accordance with this invention.
Figure 4:
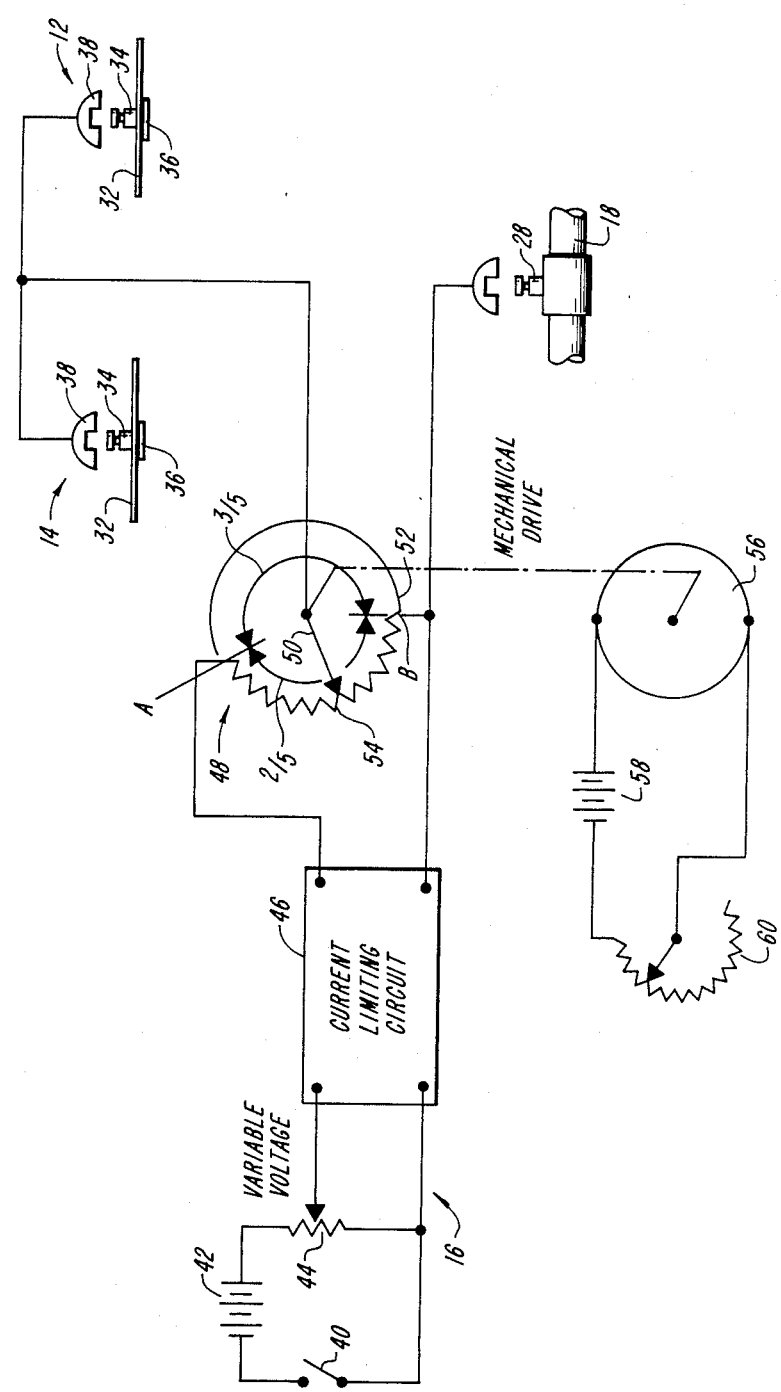
FIG. 4 is a schematic diagram of the circuit of the invention shown in FIGS. 1-3.

The control circuit 16 for impressing a pulsed charge across the electrodes is shown in FIG. 4. The circuit includes a switch 40 and a battery 42 in circuit with a voltage divider 44 which enables the operator to select the desired current to be delivered. For the safety of the patient, a current limiting circuit represented by box 46 is connected across the output of the voltage divider. No more than 100 milliamperes should pass through the circuit across the electrodes. A saw-tooth generator in the form of a motor driven continuously rotating potentiometer 48 is connected across the voltage divider to produce the saw-tooth signal shown in FIG. 5. The internal electrode 10 and the external electrodes 12 and 14 in turn are connected to the sweep 50 and resistor ring 52 of potentiometer 48.

The resistance 54 of ring 52 extends about two-fifths of the ring. As a result, during the two-fifths of the cycle as the sweep moves from point A to point B, the signal steadily increases in magnitude, but it drops off sharply at point B and remains at zero for the remaining three-fifths of the cycle.

The potentiometer 48 is driven by motor 56 energized by battery 58 and controlled by rheostat 60. The speed of the motor may be varied so as to selectively turn the potentiometer at from 10 to 18 rpm. It will be appreciated that this arrangement insures that the pulsed charge will have a duration of two-fifths of the cycle, or 2 seconds if the cycle time is 5 seconds (12 rpm), and during the remaining three-fifths of the cycle (3 seconds) the charge will be zero. This sequence is suggested in the chart of FIG. 5. When the pulse rate is varied from 12 per minute to some other value, the length of each pulse and the intervals between successive pulses are proportionally varied. The magnitude of each pulse may be varied up to a limit of 100 milliamperes.

In accordance with the present invention, as the pulses are passed between the internal and external electrodes, the thoracic activity expands to create a negative pressure, and inspiration occurs. Between pulses, the muscles relax to cause exhalation. This normal way of breathing does not inhibit blood flow in the lungs and to the heart.

In accordance with the method of this invention, a pulsing charge is directed between an internal electrode placed in the esophagus and external electrodes placed on the chest in the region of the nipples, and above the rib cage, and the charge serves to stimulate the diaphragm muscles so as to cause the lungs to expand. This technique is practiced without requiring any surgical procedure and therefore may be conducted by a paramedic. As the system is portable, the procedure may be carried out at any location. It does not require large, heavy equipment such as oxygen bottles, etc. The person administering the care may very quickly insert the internal electrode in place, affix the external electrodes at the desired locations and activate the pulsing circuit by closing the switch.

Having described this invention in detail, those skilled in the art will appreciate that numerous modifications may be made of this invention without departing from its spirit. Therefore, it is not intended that the scope of this invention be limited to the specific embodiment illustrated and described. Rather, the scope of the invention is to be determined by the appended claims and their equivalents.

I claim:

1. Medical apparatus for inducing breathing in humans comprising
    an internal elongated first electrode member for insertion into the esophagus and having a distal end carrying a plurality of spaced apart ring contacts to be positioned in the lower portion of the esophagus,
    ECG-type external second and third electrode members for placement on the chest in the region of the nipples and above the rib cage,
    and electrical circuit means connected to the three electrode members for passing a current between the internal and external electrode members at a rate of between 10 and 18 pulses per minute with each pulse having a duration of approximately two seconds and of a maximum value of approximately 100 milliamperes.

2. Medical apparatus for inducing breathing as defined in claim 1 further characterized by said ring contacts being connected in series and said second and third electrode members being connected in parallel.

3. Medical apparatus as defined in claim 1 wherein said electrical circuit means includes means for increasing the magnitude of each pulse from zero to maximum value gradually over the duration of each pulse.

4. Medical apparatus for inducing breathing in humans comprising a first internal electrode member for insertion into the esophagus of a patient and having a distal end with an electrical contact to be positioned in the lower third of the esophagus, second and third external electrode members having contacts for placement over the left and right sides of the chest adjacent the diaphragm muscles, and electrical circuit means connected to the three electrode members for imposing a pulsed charge between the internal and external electrodes of approximately two seconds duration and approximately three seconds between pulses and limited to a maximum of approximately 100 milliamperes for stimulating the daiphragm to cause the patient to breath.

5. A medical apparatus as defined in claim 3 further characterized by said electrical circuit means including means for varying the pulse rate from approximately 10 to 18 pulses per minute.

6. Medical apparatus as defined in claim 4 wherein said electrical circuit means includes means for increasing each pulse gradually during its duration.

7. A method of stimulating breathing in humans comprising the steps of positioning a non-invasive internal electrode in the esophagus of the patient and two external electrodes on the surface of the patient's skin one on each side adjacent the diaphragm muscles, and imposing a pulsed charge between the internal and the external electrodes which will stimulate the diaphragm muscle to cause expansion of the thoracic cavity at the rate of between 10 and 18 times per minute.

8. A method of stimulating breathing in humans as defined in claim 7 further characterized by adhering the external electrodes to the skin by an electrically conductive adhesive.

9. A method of stimulating breathing in humans as defined in claim 7 further characterized by causing each pulse to increase in magnitude from zero to maximum over a period of approximately two seconds and delaying each pulse to start approximately three seconds after the preceding pulse ends.

10. A method of stimulating breathing in humans as defined in claim 5 further characterized by using ECG-type electrodes as the two external electrodes.

11. A method of stimulating breathing in humans comprising the steps of positioning adjacent the sides of the diaphragm muscles of a patinet a non-invasive internal electrode within the body and electrode means outside the body of the patient, and imposing a pulsed charge between the internal electrode and electrode means for causing the thoracic cavity to expand with each pulse and relax between pulses at the rate of between 10 and 18 times per minute.

12. A method as defined in claim 11 wherein the magnitude of each pulsed charge is increased gradually to a maximum value followed by an abrupt secession of the charge.

13. A method as defined in claim 12 wherein a period of no pulsed charge is interposed between the pulsed charges, and wherein the duration of each pulsed charge is approximately two seconds and a period of approximately three seconds is interposed between the pulsed charges.

* * * * *